United States Patent [19]

Stanaback et al.

[11] 4,046,719

[45] Sept. 6, 1977

[54] FLAME-RETARDANT RESINOUS COMPOSITIONS CONTAINING TRIHALONEOPENTYL HALOALKYL PHOSPHATES

[75] Inventors: Robert J. Stanaback, Gladstone, N.J.; Michael J. Reale, Southeast, N.Y.

[73] Assignee: Tenneco Chemicals, Inc., Saddle Brook, N.J.

[21] Appl. No.: 569,130

[22] Filed: Apr. 17, 1975

[51] Int. Cl.² .................................. C08K 5/52
[52] U.S. Cl. ..................... 260/2.5 FP; 106/177; 260/45.7 P; 260/953; 260/963; 260/965
[58] Field of Search ............. 260/45.7 P, 963, 965, 260/953, 2.5 FP; 106/177

[56] References Cited

U.S. PATENT DOCUMENTS 3,706,822   12/1972   Caldwell ..................... 260/965

*Primary Examiner*—Sandra M. Person
*Attorney, Agent, or Firm*—Evelyn Berlow

[57] ABSTRACT

Flame-retardant resinous compositions comprise an organic polymer and a phosphate that has the structural formula

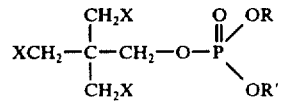

wherein each X represents bromine or chlorine; R represents haloalkyl having 2 to 4 carbon atoms and 1 to 5 bromine and/or chlorine atoms, phenyl, or trihaloneopentyl; and R' represents haloalkyl having 2 to 4 carbon atoms and 1 to 5 bromine and/or chlorine atoms.

17 Claims, No Drawings

FLAME-RETARDANT RESINOUS COMPOSITIONS CONTAINING TRIHALONEOPENTYL HALOALKYL PHOSPHATES

This invention relates to trihaloneopentyl haloalkyl phosphates and to flame-retardant resinous compositions that contain these compounds.

There is a growing concern regarding the fire resistance of plastics and other materials that are used in private homes, public buildings, military and industrial applications, and public and private transportation. In many cases, standards of flame-retardance have been established for these materials; in all probability, more stringent standards will have to be met in the future.

A number of organic and inorganic compounds have been suggested as flame-retardants for resinous compositions, but none has proven to be entirely satisfactory for this purpose. Some do not provide the necessary flame retardance, while others have an adverse effect on the properties of the compositions. For example, resinous compositions that contain a triaryl phosphate, a trialkyl phosphate, or an aryl alkyl phosphate often have unsatisfactory processing characteristics and heat and light stability. Phosphates that contain bromine or chlorine are known to impart flame resistance to normally-flammable resinous compositions, but they are often thermally unstable and when subjected to elevated temperatures during extrusion, molding, and other fabrication they decompose to form free acids that have a deleterious effect on the physical and mechanical properties of the compositions and that cause corrosion of the processing equipment.

In accordance with this invention, it has been found that certain trihaloneopentyl haloalkyl phosphates have excellent thermal and hydrolytic stability and other properties that make them valuable as flame retardants for normally-flammable resinous compositions.

The flame-retardant compounds of this invention have the structural formula

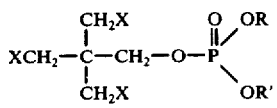

wherein each X represents bromine or chlorine; R represents haloalkyl having 2 to 4 carbon atoms and 1 to 5 halogen atoms selected from the group consisting of bromine, chlorine, and mixtures thereof, phenyl, or —CH$_2$—C(CH$_2$X)$_3$; and R' represents haloalkyl having 2 to 4 carbon atoms and 1 to 5 halogen atoms selected from the group consisting of bromine, chlorine, and mixtures thereof.

Illustrative of these compounds are the following: tribromoneopentyl bis(1,3-dichloropropyl) phosphate, tribromoneopentyl bis(2,3-dibromopropyl) phosphate, tribromoneopentyl bis(trichlorobutyl) phosphate, dichlorobromoneopentyl bis(pentachlorobutyl) phosphate, bis(tribromoneopentyl)chloroethyl phosphate, bis(tribromoneopentyl) 2-chloropropyl phosphate, bis(tribromoneopentyl) pentabromobutyl phosphate, trichloroneopentyl phenyl dibromobutyl phosphate, trichloroneopentyl phenyl tetrabromopropyl phosphate, bis(trichloroneopentyl)dibromopropyl phosphate, chlorodibromoneopentyl trichloroethyl dichlorodibromobutyl phosphate, tribromoneopentyl phenyl dibromoethyl phosphate, dichlorobromoneopentyl phenyl trichlorodibromopropyl phosphate, dichlorobromoneopentyl bis(tetrachlorobromopropyl) phosphate, and the like.

A group of trihaloneopentyl haloalkyl phosphates have been found to be particularly valuable as the flame-retardant in rigid and flexible polyurethane foams because they impart non-scorch and non-drip characteristics to the foams and they promote char formation during flaming. These phosphates have the structural formula

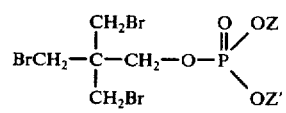

wherein Z represents chloroalkyl having 2 to 4 carbon atoms and 1 or 2 chlorine atoms, phenyl, or —CH$_2$—(CH$_2$Br)$_3$ and Z' represents chloroalkyl having 2 to 4 carbon atoms and 1 or 2 chlorine atoms.

Examples of these preferred tribromoneopentyl chloroalkyl phosphates are tribromoneopentyl bis(1,3-dichloropropyl) phosphate, tribromoneopentyl bis(2-chloropropyl) phosphate, tribromoneopentyl bis(-chloroethyl) phosphate, tribromoneopentyl phenyl 1,3-dichloropropyl phosphate, tribromoneopentyl phenyl dichlorobutyl phosphate, bis(tribromoneopentyl) chloroethyl phosphate, bis(tribromoneopentyl) 1,3-dichloropropyl phosphate, bis(tribromoneopentyl) dichlorobutyl phosphate, and the like.

A single trihaloneopentyl haloalkyl phosphate or mixture of two or more of these compounds can be used to impart flameretardance to normally-flammable resinous compositions.

The tribromoneopentyl haloalkyl phosphates may be prepared by any suitable and convenient process. For example, they may be prepared by reacting a trihaloneopentyl alcohol with phosphorus oxychloride and further reacting the resulting phosphorus-containing ester with epichlorohydrin or with an alkylene oxide. The esterification reactions are generally carried out at a temperature between about 30° and 150° C. An esterification catalyst, such as magnesium oxide and/or zinc chloride, may be used.

The trihaloneopentyl alcohols that may be used in the preparation of the phosphates of this invention have the structural formula

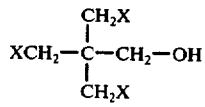

wherein each X represents bromine or chlorine. They include tribromoneopentyl alcohol, dibromochloroneopentyl alcohol, bromodichloroneopentyl alcohol, trichloroneopentyl alcohol, and mixtures thereof.

The tribromoneopentyl haloalkyl phosphates can be used to impart flame-retardance to a wide variety of normally-flammable organic polymers. While they are particularly well suited for use in compositions that are processed at temperatures below 200° C., they can also be used in compositions that are processed at higher temperatures for relatively short periods of time. Illustrative of the organic polymers that may be present in the flame-retardant compositions of this invention are polyurethanes including flexible and rigid foams; vinyl chloride homopolymers and vinyl chloride copolymers with, for example, vinyl acetate, vinyl butyrate, ethylene, methyl methacrylate, or acrylonitrile; cellulose esters and ethers; polyolefins including homopolymers and copolymers of ethylene, propylene, and isobutylene; vinyl acetate homopolymers and vinyl acetate copolymers with, for example, ethylene, methyl methacrylate, acrylonitrile or vinylidene chloride; styrene homopolymers and styrene copolymers with, for example, acrylonitrile or butadiene; polyesters; polyphenyl ethers; polycarbonates; polyamides; polyoxymethylenes; acrylic homopolymers and copolymers prepared from such monomers as acrylic acid, methyl methacrylate, and ethyl acrylate; polyepoxides; and mixtures thereof. The trihaloneopentyl haloalkyl phosphates are particularly effective in flexible and rigid polyurethane foams, in plasticized polyvinyl chloride compositions, and in cellulose acetate compositions.

The trihaloneopentyl haloalkyl phosphates can be incorporated in the resinous compositions by any convenient procedure. For example, they can be mixed with the polymer in a mill or extruder, or they can be added to a resin solution that is to be cast as a film. They can be incorporated into polyurethane compositions by mixing them with the polyol before it is reacted with the polyisocyanate.

The amount of the trihaloneopentyl haloalkyl phosphate that is incorporated into the resinous compositions is that which will impart the desired degree of flame retardance to the compositions without adversely affecting their physical properties. In most cases, it is necessary to add an amount of the flameretardant that will provide at least 0.5% by weight of phosphorus in order to obtain the desired level of flame-retardance. Flameretardant polyurethane foams result when from 5 to 50 parts of a trihaloneopentyl haloalkyl phosphate is used per 100 parts by weight of polyol. Compositions containing vinyl halide polymers, cellulose esters, polyesters, or other organic polymers generally require the use of from 5 to 50 parts, and preferably 10 to 25 parts, by weight of trihaloneopentyl haloalkyl phosphate per 100 parts by weight of the polymer.

In addition to the organic polymer and the trihaloneopentyl haloalkyl phosphate, the flame-retardant compositions may contain fillers, pigments, dyes, stabilizers, lubricants, plasticizers, solvents, and other additives in the amounts ordinarily used for these purposes.

The invention is further illustrated by the following examples.

EXAMPLE 1

Tribromoneopentyl alcohol (417 grams, 1.25 moles) and 0.9 gram of magnesium oxide were heated to 60°–70° C. in a flask fitted with a stirrer, a dropping funnel, a reflux condenser, and a water trap for hydrogen chloride absorption. The mixture was stirred and maintained at a temperature below 80° C. while 192.5 grams (1.25 moles) of phosphorus oxychloride was added to it over a period of 2 hours. The reaction mixture was then slowly heated to 140° C. During the heating period, 46 grams (1.26 moles) of hydrogen chloride was collected in the water trap.

The reaction mixture was cooled to 105° C. and then maintained at a temperature in the range of 105°–115° C. while 232 grams (2.5 moles) of epichlorohydrin was added to it. Following the addition of the epichlorohydrin, the reaction mixture was stirred at 105°–110° C. until its acid number was less than 1 mg. KOH/gram. When the mixture had cooled to 95° C., 4 grams of 30% hydrogen peroxide was added to it, and it was stirred at 95°–105° C. for 30 minutes.

The reaction product was washed by stirring it with 250 grams of 8% sodium carbonate solution at 90°–95° C. for 1 hour and then with 250 grams of water at 90°–95° C. for 1 hour. The product was dried by heating it under vacuum to 125° C./10 mm. It was treated with 3.5 grams of diatomaceous earth at 95°–105° C. for 10 minutes and filtered.

There was obtained 714.5 grams (1.13 moles) of tribromoneopentyl bis(1,3-dichloropropyl) phosphate, which was found to contain 4.9% P and 10.9 meq./g. of halogen (calculated, 4.9% P and 11.2 meq./g. of halogen) and to have an acid number of 0.25 mg. KOH/gram.

EXAMPLE 2

To a mixture of 666 grams (2.0 moles) of tribromoneopentyl alcohol and 1 gram of magnesium oxide at 60° C. was added dropwise over a period of 1.5 hours 153.5 grams (1.0 mole) of phosphorus oxychloride. The reaction mixture was heated to 150° C. over a period of two hours and then cooled to 90° C. It was stirred and maintained at 95°–110° C. for 1.5 hours while 92.5 grams (1.0 mole) of epichlorohydrin was added to it and then heated at 105° C. for 3.5 hours to reduce its acid number to 1.2 mg. KOH/gram.

The product to which 3.5 grams of 30% hydrogen peroxide had been added was heated at 95°–100° C. for 30 minutes and then washed with 300 ml. portions of 8% sodium carbonate solution, 0.5% sodium carbonate solution, and water, each washing being carried out for 1 hour at 95°–100° C. The product was dried by heating it to 140° C./35 mm. absolute and sparging it with nitrogen for 3.5 hours.

There was obtained 713 grams (85.2% of theory) of bis(tribromoneopentyl) 1,3-dichloropropyl phosphate, which was found to contain 3.2% P and 9.5 meq./gram of halogen (calculated, 3.7% and 9.5 meq./gram of halogen) and to have an acid number of 7.4 mg. KOH/gram and a hydroxyl number of 28.9.

EXAMPLE 3

Tribromoneopentyl alcohol (666 grams, 2.0 moles) and 0.5 gram of magnesium oxide were heated to 60° C. and maintained at this temperature while 153.5 grams (1.0 mole) of phosphorus oxychloride was added dropwise to it over a period of 2 hours. The reaction mixture was heated to 140° C. over a period of 3 hours during which 75 grams of hydrogen chloride was evolved.

The reaction mixture was cooled to 95° C., and 60 grams (1.03 moles) of propylene oxide was added dropwise to it over a period of 2.5 hours. It was heated at 110° C. for 1.5 hours to reduce its acid number to 0.68 mg. KOH/gram. Then after the addition of 10 grams (0.17 mole) of propylene oxide, it was heated under reflux conditions at 85°–95° C. for 45 minutes.

The reaction product was diluted with 100 ml. of toluene and washed first with 300 ml. of 5% sodium sulfite solution, then 200 ml. of 8% sodium carbonate solution, and finally 300 ml. of water, each washing being carried out for 30 minutes at 95° C. The product was dried by heating it under vacuum to 120° C./10 mm. and then sparging it with nitrogen for 1 hour at 120° C. It was filtered at 110° C.

There was obtained 657 grams (82% of theory) of bis(tribromoneopentyl) 2-chloropropyl phosphate, which was found to contain 3.9% P and 8.70 meq./g. of halogen (calculated, 3,85% P and 8.70 meq./g. of halogen) and to have an acid number of 0.3 mg. KOH/gram.

EXAMPLE 4

Tribromoneopentyl alcohol (500 grams, 1.5 moles) and 0.8 gram of magnesium oxide were heated to 60° C. and maintained at this temperature while 231.5 grams (1.5 moles) of phosphorus oxychloride was added dropwise to it over a period of 2 hours. The reaction mixture was heated to 138° C. over a period of 3 hours. When the evolution of hydrogen chloride ceased, the reaction mixture was cooled to 95° C. Then 210 grams (3.62 moles) of propylene oxide was added to it dropwise over a period of 2.5 hours. The reaction mixture was then heated under reflux conditions at 92° C. for 1 hour to reduce its acid number 0.12 mg. KOH/gram.

The reaction product to which 5 grams of 30% hydrogen peroxide had been added was stirred at 90°-95° C. for 30 minutes and then washed with 200 ml. portions of 5% sodium sulfite solution, water, 8% sodium carbonate solution, and finally water, each washing being carried out for 30 minutes at 95° C. The product was dried by heating it to 125° C./5mm., sparged with nitrogen for 3 hours, and filtered at 110° C.

There was obtained 728 grams (84.8% of theory) of tribromoneopentyl bis(2-chloropropyl) phosphate, which was found to contain 5.4% P and 8.6 meq./gram of halogen (Calculated, 5.5% P and 8.8 meq./gram of halogen) and to have an acid number of 0.4 mg. KOH/gram and a hydroxyl number of 5.6.

EXAMPLE 5

To a mixture of 94 grams (1 mole) of phenol, 333 grams (1.0 mole) of tribromoneopentyl alcohol, 0.50 gram of magnesium oxide, and 0.50 gram of zinc chloride which had been heated to 50° C. was added dropwise over a period of 1 hour 153.5 grams (1.0 mole) of phosphorus oxychloride. The reaction mixture was heated to 135° C. over a period of 3.5 hours. After 98 grams (1.06 moles) of epichlorohydrin had been added dropwise to it over a 1.5 hour period while it was stirred and maintained at 100°-115° C., the reaction mixture was heated at 110° C. for 2 hours and then at 95°-100° C. for 30 minutes with 3 grams of 30% hydrogen peroxide.

The product was washed with 300 ml. of 8% sodium carbonate solution at 90° C. for 30 minutes and then with 300 ml. of hot water. It was dried at 120° C./25 mm. absolute. There was obtained 516 grams (86.4% of theory) of tribromoneopentyl phenyl 1,3-dichloropropyl phosphate, which contained 5.26% P and 8.1 meq./gram of halogen (calculated, 5.23% P and 8.3 meq./gram of halogen) and had an acid number of 1.7 mg. KOH/gram.

EXAMPLE 6

The following procedure was used to evaluate the compounds of Exaples 1-5 as the flame-retardant in a flexible polyurethane foam:

A mixture of 200 grams aof a polyether that had a hydroxyl number of 56 (Polyol LG-56), 30 grams of one of the phosphates of this invention, 2.5 grams of a silicone surfactant (L 5710), 0.6 gram of triethylenediamine (Dabco 33-LV), 0.1 gram of N-ethylmorpholine, and 7.4 grams of water was homogenized for 4.5 minutes. After the addition of 0.5 gram of stannous octoate, the mixture was homogenized for 30 seconds. Then 96.4 grams of tolylene diisocyanate (80/20 mixture of 2,4-and 2,6-isomers) was added, and, after homogenization for 5 seconds, the mixture was poured into a mold and allowed to rise. The resulting foam was cured in a circulating air oven at 150° C. for 5 minutes, cut into 6 × 2 × 0.5 specimens, and tested for flammability according to "Method of Test for Flammability of Plastic Foams and Sheeting", ASTM-1692-74. The results obtained are summarized in Table I. For comparative purposes, a foam that contained a commercially-available flame-retardant material tris(1,3-dichloropropyl) phosphate was included in the tests.

EXAMPLE 7

The following procedure was used to evaluate tribromoneopentyl bis(1,3-dichloropropyl) phosphate as the flame-retardant in a clear polyvinyl chloride composition:

The following materials were mixed together:

|  | Parts by Weight |
|---|---|
| Polyvinyl chloride (relative viscosity - 2.4, 1% in cyclohexane) | 100.0 |
| Ba/Cd/Zn stabilizer (NUOSTABE V-1397) | 3.0 |
| Stearic Acid | 0.5 |

Table I

| Flame Retardant | Level (parts/100 parts polyol) | Average Time of Burn (sec.) | Average Extent of Burn (mm.) |
|---|---|---|---|
| Product of Ex. 1 | 15 | 24.2 | 26.6 |
| Product of Ex. 2 | 15 | 26.8 | 32.8 |
| Product of Ex. 3 | 15 | 23.8 | 29.0 |
| Product of Ex. 4 | 15 | 25.0 | 27.6 |
| Product of Ex. 5 | 15 | 23.4 | 33.0 |
| Tris(1,3-dichloropropyl) phosphate | 15 | 33.8 | 40.4 |

|  | Parts by Weight |
|---|---|
| Epoxidized soybean oil | 5.0 |
| Dioctyl phthalate | 35.0 |
| Tribromoneopentyl bis(1,3-dichloropropyl) phosphate | 10.0 |

The mixture was milled at 160° C. on a two roll mill for 5 minutes and removed from the mill as a sheet 0.045 inch thick. Specimens cut from the sheet were press molded to form specimens that were 0.07 inch thick.

The Limiting Oxygen Index (LOI) of the composition as determined by the procedure described in ASTM-D-2863 was 25.7.

A comparative composition that contained no flame-retardant had a Limiting Oxygen Index of 22.9.

EXAMPLE 8

A mixture of 22.5 grams of cellulose triacetate, 2.5 grams of tribromoneopentyl bis(1,3-dichloropropyl) phosphate, and 270 grams of a 91/1 mixture of dichloromethane and methanol was rolled in a sealed container for 14 hours at ambient temperature. The mixture was cast as a film 0.05 inch thick and dried at 80° C. The Limiting Oxygen Index as determined by ASTM-D-2863 was 22.5.

A comparative composition that contained tris(2,3-dibromopropyl) phosphate as the flame-retardant had an LOI of 21.6, whereas one that contained no flame-retardant had an LOI of 17.6.

What is claimed is:

1. A phosphate having the structural formula $$\text{XCH}_2-\underset{\underset{\text{CH}_2\text{X}}{|}}{\overset{\overset{\text{CH}_2\text{X}}{|}}{\text{C}}}-\text{CH}_2-\text{O}-\overset{\text{O}}{\underset{}{\text{P}}}\overset{\text{OR}}{\underset{\text{OR}'}{\diagdown}}$$

wherein each X represents bromine or chlorine; R represents haloalkyl having 2 to 4 carbon atoms and 1 to 5 halogen atoms selected from the group consisting of chlorine, bromine, and mixtures thereof, phenyl, or —CH$_2$—C(CH$_2$X)$_3$; and R' represents haloalkyl having 2 to 4 carbon atoms and 1 to 5 halogen atoms selected from the group consisting of chlorine, bromine, and mixtures thereof.

2. A phosphate as defined in claim 1 wherein each X represents bromine.

3. A phosphate as defined in claim 1 wherein R represents tribromoneopentyl.

4. A phosphate as defined in claim 1 wherein R represents chloroalkyl having 2 to 4 carbon atoms and 1 to 2 chlorine atoms.

5. The phosphate of claim 1 wherein each X represents bromine and R and R' each represents chloropropyl.

6. The phosphate of claim 1 wherein each X represents bromine, R represents tribromoneopentyl, and R' represents chloropropyl.

7. A flame-retardant resinous composition that comprises an organic polymer and a flame-retarding amount of a phosphate having the structural formula $$\text{XCH}_2-\underset{\underset{\text{CH}_2\text{X}}{|}}{\overset{\overset{\text{CH}_2\text{X}}{|}}{\text{C}}}-\text{CH}_2-\text{O}-\overset{\text{O}}{\underset{}{\text{P}}}\overset{\text{OR}}{\underset{\text{OR}'}{\diagdown}}$$

wherein each X represents bromine or chlorine; R represents haloalkyl having 2 to 4 carbon atoms and 1 to 5 halogen atoms selected from the group consisting of bromine, chlorine, and mixtures thereof, phenyl, or —CH$_2$—C(CH$_2$X)$_3$; and R' represents haloalkyl having 2 to 4 carbon atoms and 1 to 5 halogen atoms selected from the group consisting of bromine, chlorine, and mixtures thereof.

8. A flame-retardant resinous composition as defined in claim 7 wherein the organic polymer is polyurethane.

9. A flame-retardant resinous composition as defined in claim 7 wherein the organic polymer is a vinyl halide resin.

10. A flame-retardant resinous composition as defined in claim 7 wherein the organic polymer is a cellulose ester.

11. A flame-retardant resinous composition as defined in claim 7 wherein the phosphate has the structural formula $$\text{BrCH}_2-\underset{\underset{\text{CH}_2\text{Br}}{|}}{\overset{\overset{\text{CH}_2\text{Br}}{|}}{\text{C}}}-\text{CH}_2-\text{O}-\overset{\text{O}}{\underset{}{\text{P}}}\overset{\text{OZ}}{\underset{\text{OZ}'}{\diagdown}}$$

wherein Z represents chloroalkyl having 2 to 4 carbon atoms and 1 or 2 chlorine atoms, phenyl, or —CH$_2$—C(CH$_2$Br)$_3$; and Z' represents chloroalkyl having 2 to 4 carbon atoms and 1 to 2 chlorine atoms.

12. A flame-retardant resinous composition as defined in claim 11 wherein the organic polymer is a polyurethane foam.

13. A flame-retardant resinous composition as defined in claim 11 wherein the phosphate is a tribromoneopentyl chloroalkyl phosphate.

14. A flame-retardant resinous composition as defined in claim 11 wherein the phosphate is a tribromoneopentyl bis(chloropropyl) phosphate.

15. A flame-retardant resinous composition as defined in claim 11 wherein the phosphate is a tribromoneopentyl phenyl chloropropyl phosphate.

16. A flame-retardant resinous composition as defined in claim 11 wherein the phosphate is a bis(tribromoneopentyl) chloropropyl phosphate.

17. A flame-retardant resinous composition as defined in claim 11 wherein the phosphate is tribromoneopentyl bis(1,3-dichloropropyl) phosphate.

* * * * *